US008287912B2

(12) United States Patent  
Lotan et al.

(10) Patent No.: US 8,287,912 B2
(45) Date of Patent: Oct. 16, 2012

(54) USE OF STINGING CELLS/CAPSULES FOR THE DELIVERY OF ACTIVE AGENTS TO KERATINOUS SUBSTANCES

(75) Inventors: Tamar Lotan, Jordan Valley (IL); Shimon Eckhouse, Haifa (IL)

(73) Assignee: NanoCyte Inc., Wilmington, DE (US)

( * ) Notice: Subject to any disclaimer, the term of this patent is extended or adjusted under 35 U.S.C. 154(b) by 0 days.

(21) Appl. No.: 13/166,877

(22) Filed: Jun. 23, 2011

(65) Prior Publication Data

US 2011/0250245 A1    Oct. 13, 2011

Related U.S. Application Data

(60) Division of application No. 12/616,801, filed on Nov. 12, 2009, now Pat. No. 7,998,509, which is a continuation of application No. 11/328,221, filed on Jan. 10, 2006, now Pat. No. 7,632,522, which is a continuation-in-part of application No. 10/868,802, filed on Jun. 17, 2004, now Pat. No. 7,338,665, which is a division of application No. 10/406,202, filed on Apr. 4, 2003, now Pat. No. 6,923,976, which is a division of application No. 09/963,672, filed on Sep. 27, 2001, now Pat. No. 6,613,344.

(60) Provisional application No. 60/235,910, filed on Sep. 28, 2000.

(51) Int. Cl.
*A61K 35/12* (2006.01)

(52) U.S. Cl. ................. 424/520; 424/93.21; 424/401; 435/325

(58) Field of Classification Search .................. None
See application file for complete search history.

(56) References Cited

U.S. PATENT DOCUMENTS

| | | |
|---|---|---|
| 3,321,188 A | 5/1967 | Unger |
| 3,839,153 A | 10/1974 | Schuurs et al. |
| 3,850,578 A | 11/1974 | Mc Connell |
| 3,850,752 A | 11/1974 | Schuurs et al. |
| 3,853,987 A | 12/1974 | Dreyer |
| 3,879,262 A | 4/1975 | Schuurs et al. |
| 3,984,533 A | 10/1976 | Uzgiris |
| 4,034,074 A | 7/1977 | Miles |
| 4,224,013 A | 9/1980 | Davis |
| 4,666,828 A | 5/1987 | Gusella |
| 4,801,531 A | 1/1989 | Frossard |
| 5,073,488 A | 12/1991 | Matner et al. |
| 5,162,378 A | 11/1992 | Guthauser |
| 5,192,659 A | 3/1993 | Simons |
| 5,272,057 A | 12/1993 | Smulson et al. |
| 5,362,442 A | 11/1994 | Kent |
| 5,641,508 A | 6/1997 | Li et al. |
| 5,885,211 A | 3/1999 | Eppstein et al. |
| 5,885,260 A | 3/1999 | Mehl, Sr. et al. |
| 6,019,967 A | 2/2000 | Breton et al. |
| 6,022,316 A | 2/2000 | Eppstein et al. |
| 6,132,747 A | 10/2000 | Lotan |
| 6,338,837 B1 | 1/2002 | Lotan |
| 6,406,709 B1 | 6/2002 | Lotan |
| 6,416,960 B1 | 7/2002 | Bryan |
| 6,596,531 B2 | 7/2003 | Campbell et al. |
| 6,613,344 B2 | 9/2003 | Lotan et al. |
| 6,613,744 B2 | 9/2003 | Wozney et al. |
| 6,923,976 B2 | 8/2005 | Lotan et al. |
| 7,338,665 B2 | 3/2008 | Lotan et al. |
| 7,611,723 B2 | 11/2009 | Lotan et al. |
| 8,062,660 B2 | 11/2011 | Lotan et al. |
| 2001/0004715 A1 | 6/2001 | Duran et al. |
| 2002/0039592 A1 | 4/2002 | Lotan et al. |
| 2003/0189850 A1 | 10/2003 | Sasaki et al. |
| 2003/0202995 A1 | 10/2003 | Lotan et al. |
| 2004/0235143 A1 | 11/2004 | Sasaki et al. |
| 2005/0181978 A1 | 8/2005 | Rojkjaer et al. |
| 2006/0039897 A1 | 2/2006 | Lotan et al. |
| 2006/0099272 A1 | 5/2006 | Lotan |
| 2006/0099273 A1 | 5/2006 | Lotan |
| 2006/0159769 A1 | 7/2006 | Lotan et al. |
| 2006/0234203 A1 | 10/2006 | Lotan et al. |
| 2007/0160546 A1 | 7/2007 | Lotan et al. |
| 2010/0055058 A1 | 3/2010 | Lotan et al. |
| 2011/0070224 A1 | 3/2011 | Lotan et al. |

FOREIGN PATENT DOCUMENTS

| | | |
|---|---|---|
| EP | 1519755 | 4/2005 |
| WO | WO 98/29134 | 7/1998 |
| WO | WO 99/44507 | 9/1999 |
| WO | WO 99/44508 | 9/1999 |
| WO | WO 99/44637 | 9/1999 |
| WO | WO 99/44638 | 9/1999 |
| WO | WO 00/03758 | 1/2000 |
| WO | WO 00/04821 | 2/2000 |
| WO | WO 00/04832 | 2/2000 |
| WO | WO 00/15102 | 3/2000 |
| WO | WO 01/37778 | 5/2001 |
| WO | WO 02/26191 | 4/2002 |
| WO | WO 03/079967 | 10/2003 |
| WO | WO 2006/048864 | 5/2006 |
| WO | WO 2006/048865 | 5/2006 |
| WO | WO 2006/111960 | 10/2006 |

OTHER PUBLICATIONS

Notice of Allowance Dated Aug. 16, 2011 From the US Patent and Trademark Office Re.: U.S. Appl. No. 11/374,969.
"Skin, Hair, and Nails", http://web.archive.org/web.20030404084846/www.kidshealth.org/PageManager.jsp?dn=Kidshealth&lic=1&ps=107&cat_id-20090&article_set-20552, p. 1-7, 2003. Communication Pursuant to Article 94(3) EPC Dated Feb. 2, 2010 From the European Patent Office Re.: Application No. 01976586.6.
Communication Pursuant to Article 94(3) EPC Dated Dec. 17, 2008 From the European Patent Office Re.: Application No. 01976586.6.
International Preliminary Report on Patentability Dated Dec. 11, 2008 From the International Bureau of WIPO Re.: Application No. PCT/IL2006/000465.
International Preliminary Report on Patentability Dated May 18, 2007 From the International Bureau of WIPO Re.: Application No. PCT/IL2005/001127.

(Continued)

Primary Examiner — Laura Schuberg (57) ABSTRACT

A composition of matter comprising an agent beneficial to a non-skin keratinous substance and at least one stinging capsule and methods of use are disclosed.

6 Claims, 2 Drawing Sheets

OTHER PUBLICATIONS

International Search Report Dated Jun. 22, 2006 From the International Searching Authority Re.: Application No. PCT/IL05/01127.
International Search Report Dated Jun. 24, 2008 From the International Searching Authority Re.: Application No. PCT/IL2006/000465.
Notice of Allowance Dated Aug. 6, 2009 From the US Patent and Trademark Office Re.: U.S. Appl. No. 11/328,221.
Notice of Allowance Dated Jun. 19, 2009 From the US Patent and Trademark Office Re.: U.S. Appl. No. 10/507,692.
Notice of Allowance Dated Aug. 23, 2010 From the US Patent and Trademark Office Re.: U.S. Appl. No. 11/374,969.
Notice of Allowance Dated Mar. 24, 2011 From the US Patent and Trademark Office Re.: U.S. Appl. No. 12/616,801.
Office Action Dated Sep. 2, 2010 From the Israeli Patent Office Re.: Application No. 155097 and Its Translation Into English.
Office Action Dated Jun. 4, 2008 From the Israeli Patent Office Re.: Application No. 164191.
Office Action Dated Jul. 7, 2008 From the Israeli Patent Office Re.: Application No. 155097.
Office Action Dated May 7, 2010 From the US Patent and Trademark Office Re.: U.S. Appl. No. 11/374,969.
Office Action Dated Feb. 15, 2009 From the Israeli Patent and Trademark Office Re.: Application No. 155097 and Its Translation Into English.
Office Action Dated Feb. 16, 2010 From the US Patent and Trademark Office Re.: U.S. Appl. No. 11/374,969.
Office Action Dated Jun. 20, 2007 From the Israeli Patent Office Re.: Application No. 155097.
Office Action Dated Nov. 23, 2009 From the Israeli Patent Office Re.: Application No. 155097 and Its Translation Into English.
Office Action Dated Feb. 27, 2011 From the Israeli Patent Office Re.: Application No. 164191 and Its Translation Into English.
Office Action Dated Jul. 29, 2010 From the Israel Patent Office Re. Application No. 199236 and Its Translation Into English.
Office Action Dated Jul. 29, 2010 From the Israeli Patent Office Re.: Application No. 164191 and Its Translation Into English.
Official Action Dated Nov. 1, 2007 From the US Patent and Trademark Office Re.: U.S. Appl. No. 11/328,221.
Official Action Dated Oct. 4, 2006 From the US Patent and Trademark Office Re.: U.S. Appl. No. 10/868,802.
Official Action Dated Oct. 4, 2007 From the US Patent and Trademark Office Re.: U.S. Appl. No. 10/507,692.
Official Action Dated Apr. 6, 2009 From the US Patent and Trademark Office Re.: U.S. Appl. No. 11/374,969.
Official Action Dated Jun. 6, 2006 From the US Patent and Trademark Office Re.: U.S. Appl. No. 10/981,522.
Official Action Dated Aug. 8, 2006 From the US Patent and Trademark Office Re.: U.S. Appl. No. 11/374,969.
Official Action Dated Aug. 9, 2007 From the US Patent and Trademark Office Re.: U.S. Appl. No. 11/374,969.
Official Action Dated Oct. 9, 2008 From the US Patent and Trademark Office Re.: U.S. Appl. No. 11/328,221.
Official Action Dated Jul. 10, 2008 From the US Patent and Trademark Office Re.: U.S. Appl. No. 11/108,662.
Official Action Dated Jul. 10, 2009 From the US Patent and Trademark Office Re.: U.S. Appl. No. 11/108,662.
Official Action Dated Apr. 11, 2011 From the US Patent and Trademark Office Re.: U.S. Appl. No. 11/374,969.
Official Action Dated Apr. 13, 2009 From the US Patent and Trademark Office Re.: U.S. Appl. No. 11/328,221.
Official Action Dated Aug. 13, 2007 From the US Patent and Trademark Office Re.: U.S. Appl. No. 11/108,662.
Official Action Dated Dec. 15, 2006 From the US Patent and Trademark Office Re.: U.S. Appl. No. 11/328,221.
Official Action Dated Jul. 17, 2008 From the US Patent and Trademark Office Re.: U.S. Appl. No. 11/328,221.
Official Action Dated Nov. 17, 2008 From the US Patent and Trademark Office Re.: U.S. Appl. No. 10/507,692.
Official Action Dated Jun. 18, 2010 From the US Patent and Trademark Office Re.: U.S. Appl. No. 12/616,801.
Official Action Dated Feb. 20, 2008 From the US Patent and Trademark Office Re.: U.S. Appl. No. 11/374,969.
Official Action Dated Sep. 20, 2007 From the US Patent and Trademark Office Re.: U.S. Appl. No. 10/981,522.
Official Action Dated Jan. 24, 2008 From the US Patent and Trademark Office Re.: U.S. Appl. No. 10/507,692.
Official Action Dated Sep. 24, 2010 From the US Patent and Trademark Office Re.: U.S. Appl. No. 12/616,801.
Official Action Dated Apr. 25, 2008 From the US Patent and Trademark Office Re: U.S. Appl. No. 10/981,498.
Official Action Dated Jul. 26, 2007 From the US Patent and Trademark Office Re.: U.S. Appl. No. 10/981,498.
Official Action Dated Feb. 27, 2007 From the US Patent and Trademark Office Re.: U.S. Appl. No. 11/374,969.
Official Action Dated Mar. 27, 2009 From the US Patent and Trademark Office Re.: U.S. Appl. No. 10/507,692.
Official Action Dated Apr. 28, 2006 From the US Patent and Trademark Office Re.: U.S. Appl. No. 10/868,802.
Official Action Dated Dec. 28, 2007 From the US Patent and Trademark Office Re.: U.S. Appl. No. 10/981,522.
Official Action Dated Jul. 29, 2008 From the US Patent and Trademark Office Re.: U.S. Appl. No. 11/374,969.
Official Action Dated Nov. 29, 2006 From the US Patent and Trademark Office Re.: U.S. Appl. No. 10/981,522.
Official Action Dated Mar. 30, 2007 From the US Patent and Trademark Office Re.: U.S. Appl. No. 11/328,221.
Official Action Dated May 30, 2006 From the US Patent and Trademark Office Re.: U.S. Appl. No. 10/981,498.
Official Action Dated Nov. 30, 2006 From the US Patent and Trademark Office Re.: U.S. Appl. No. 10/981,498.
Official Action Dated Jan. 31, 2008 From the US Patent and Trademark Office Re.: U.S. Appl. No. 11/108,662.
Response Dated Dec. 9, 2009 to Official Action of Jul. 10, 2009 From the US Patent and Trademark Office Re.: U.S. Appl. No. 11/108,662.
Response Dated Aug. 10, 2010 to Phone Conversation of Aug. 1, 2010 With the Examiner Re. Application No. 155097.
Response Dated Aug. 10, 2010 to Phone Conversation of Aug. 1, 2010 With the Examiner Re. Application No. 199236.
Response Dated Jul. 14, 2010 to Official Action of Jun. 18, 2010 From the US Patent and Trademark Office Re.: U.S. Appl. No. 12/616,801.
Response Dated May 15, 2011 to Office Action of Feb. 27, 2011 From the Israeli Patent Office Re.: Application No. 164191.
Response Dated Jun. 16, 2009 to Official Action of Apr. 6, 2009 From the US Patent and Trademark Office Re.: U.S. Appl. No. 11/374,969.
Response Dated May 17, 2010 to Communication Pursuant to Article 94(3) EPC of Feb. 2, 2010 From the European Patent Office Re.: Application No. 01976586.6.
Response Dated Dec. 22, 2010 to Official Action of Sep. 24, 2010 From the US Patent and Trademark Office Re.: U.S. Appl. No. 12/616,801.
Response Dated Feb. 22, 2010 to Office Action of Nov. 23, 2009 From the Israeli Patent Office Re.: Application No. 155097.
Response Dated Nov. 22, 2010 to Office Action of Jul. 29, 2010 From the Israel Patent Office Re. Application No. 199236.
Response Dated Nov. 22, 2010 to Office Action of Jul. 29, 2010 From the Israeli Patent Office Re.: Application No. 164191.
Response Dated Nov. 24, 2010 to Office Action of Sep. 2, 2010 From the Israeli Patent Office Re.: Application No. 155097.
Response Dated Feb. 26, 2010 to Office Action of Feb. 16, 2010 From the US Patent and Trademark Office Re.: U.S. Appl. No. 11/374,969.
Response Dated Dec. 30, 2009 to Office Action of Jun. 25, 2009 From the Israel Patent Office Re.: Application No. 164191.
Supplementary Partial European Search Report Dated Feb. 6, 2007 From the European Patent Office Re.: Application No. 01976586.6.
Written Opinion Dated Jun. 22, 2006 From the International Searching Authority Re.: Application No. PCT/IL05/01127.
Written Opinion Dated Jun. 24, 2008 From the International Searching Authority Re.: Application No. PCT/IL2006/000465.
Anderluh et al. "A Common Motif in Proparts of Cnidarian Toxins and Nematocyst Collagens and Its Putative Role", Biochimica et Biophysica Acta, 1476: 372-376, 2000.
Anderson et al. "A Triploblast Origin for Myxozoa?", Nature, 392(6674): 346-347, 1998.

Böttger et al. "GFP Expression in *Hydra*: Lessons From the Particle Gun", Development of Gene Evolution, 212: 302-305, 2002.
Bode "The Interstitial Cell Lineage of Hydra: A Stem Cell System That Arose Early in Evolution", Journal of Cell Science, 109: 1155-1164, 1996.
Brennecke et al. "The Lack of A Stress Response in Hydra Oligactis Is Due to Reduced Hsp70 mRNA Stability", European Journal of Biochemistry, 255: 703-709, 1998.
Chapman et al. "Cytological Studies of the Nematocysts of *Hydra*. I. Desmonemes, Isorhizas, Cnidocils, and Supporting Structures", Journal of Biophysical nad Biochemical Cytology, 5(1): 69-78, Plates 22-27, 1959.
Cikala et al. "Expression of GFP—Fusion Protein in *Hydra* to Investigate the Function of Genes Linked With Apoptosis", International Workshop—Evangelische Akademic, Tutzing/Germany, 2001.
Engel et al. "Atomic Force Microscopy: A Powerful Tool to Observe Biomolecules at Work", Trends in Cell Biology, 9:77-80, 1999.
Femadez-Alonso et al. "DNA Vaccination by Immersion and Ultrasound to Trout Viral Heamorrhagic Septicaemia Virus", Vaccine, 19: 3067-3075, 2001.
Gerke et al. "The Spatial Distribution of Cations in Nematocytes of *Hydra* Vulgaris", Hydrobiologia, 216/217: 661-669, 1991.
Godknecht et al. "Discharge and Mode of Action of the Tentacular Nematocysts of Anemonia Sulcata (Antozoa: Cnidaria)", Marine Biology, 100: 83-92, 1988.
Heeger et al. "Protection of Human Skin Against Jellyfish (*Cyanea Capillata*) Stings", Marine Biology, 113: 669-678, 1992. Abstract.
Hidaka "Mechanism of Nematocyst Discharge and Its Cellular Control", Advances in Comparative and Environment Physiology, 15(Chap.2): 45-76, 1993.
Hidaka et al. "Effects of Calcium on the Mechanical Properties of the Capsule Wall of Isolated Nematocysts From *Calliactis polypus*", Comparisons in Biochemistry and Physiology, 107A(1): 31-36, 1994.
Hiroshi et al. "Chemical Characterization of the Nematocyst Toxin From the Hawaiian Jellyfish *Carybdea alata*", Symposium on the Chemistry of Natural Products, Symposium Papers, 42: 391-396, 2000. Abstract.
Holstein et al. "An Ultrahigh-Speed Analysis of Exocytosis: Nematocyst Discharge", Science, New Series, 223(4638): 830-833, 1984.
Hyde "Skin, Hair, and Nails", The Nemours Foundation, Kidshealth, Retrieved From the Internet, p. 1-7, Apr. 21, 2001.
Kass-Simon et al. "The Behavioral and Developmental Physiology of Nematocysts", Canadian Journal of Zoology, 80: 1772-1794, 2002.
Kimball et al. "Efficacy of a Jellyfish Sting Inhibitor in Preventing Jellyfish Stings in Normal Volunteers", Wilderness and Environmental Medicine, 15: 102-108, 2004.
Koch et al. "Spinalin, A New Glycine- and Histidine-Rich Protein in Spines of *Hydra* Nematocysts", Journal of Cell Science, 111: 1545-1554, 1998.
Lohmann et al. "Silencing of Developmental Genes in *Hydra*", Developmental Biology, 214: 211-214, 1999.
Lotan et al. "Delivery of a Nematocyst Toxin", Nature, XP008041281, 375(6531): 456, Jun. 8, 1995.
Lotan et al. "Skin Protection Against Seabather's Eruption and Jellufish Sting", American Academy of Dermatology, p. 172-173, Poster Abstract.
Lotan et al. "Toxin Compartmentation and Delivery in the Cnidaria: The Nematocyst's Tubule as A Multiheaded Poisonous Arrow", The Journal of Experimental Zoology, 275(6): 444-451, 1996.
Lubbock "Chemical Recognition and Nematocyte Exitation in a Sea Anemone", Journal of Experimental Biology, 83: 283-292, 1979.
Lubbock et al. "Removal of Bound Calcium From Nematocyst Contents Causes Discharge", Nature, 290(5806): 500-501, 1981.
Marchini et al. "A Fast Centrifuge Method for Nematocyst Isolation From Pelagia Noctiluca Forskal (Cnidaria: Scyphozoa)", Rivista di Biologia, Biology Forum, 97: 505-516, 2004.
Marino et al. "Regulatory Volume Increase in Nematocytes Isolated From Acontia of Aiptasia Diaphana (Cnidaria, Anthozoa)", Cellular and Molecular Biology, 50: 533-542, 2004.

Miljkovic et al. "Cnidarian and Bilaterian Promoters Can Direct GFP Expression in Transfected *Hydra*", Development Biology, 246: 377-390, 2002.
Miljovic et al. "GFP Expression in *Hydra*", International Workshop—Evangelische Akademie, Tutzing/Germany, 2001. Abstract.
Murate et al. "*Hydra* Regeneration From Recombinant Ectodermal and Endodermal Tissue—II. Differential Stability in the Ectodermal and Endodermal Epithelial Organization", Journal of Cell Science, 110: 1155-1164, 1997.
Opalinska et al. "Nucleic-Acid Therapeutics: Basic Principles and Recent Applications", Nature Reviews: Drug Delivery, 1: 503-514, 2002.
Ozbek et al. "A Switch in Disulfide Linkage During Minicollagen Assembly in *Hydra* Nematocysts", The EMBO Journal, 20(12): 3063-3073, 2001. Abstract.
Robson "Nematocysts of Corynactis: The Activity of the Filament During Discharge", Quarterly Journal of Microscopical Science, 94(Part 3): 229-235, Sep. 1953.
Salleo et al. "Release of Free CA2 | From the Nematocysts of Aiptasia Mutabilis During the Discharge", Physiology & Zoology, 61(3): 272-279, 1988.
Sharp "RNAi and Double-Strand RNA", Genes & Development, 13: 139-141, 1999.
Siddall et al. "The Demise of A Phylum of Protists: Phylogeny of Myxozoa and Other Parasitic Cnidaria", Journal of Parasitology, 81(6): 961-967, 1995.
Smothers et al. "Molecular Evidence That the Myxozoan Protists Are Metazoans", Science, 265(5179): 1719-1721, 1994.
Stauffer et al. "Common Florida Injuries", Empulse, 8(3.2): 11-14, 2003.
Tardent "The Cnidarian Cnidocyte, A High-Tech Cellular Weaponry", BioEssays, XP00804143, 17(4): 351-362, 1995.
Tardent et al. "Morphology and Morphodynamics of the Stenotele Nematocyst of *Hydra* Attenuata Pall (Hydrozoa, Cnidaria)", Cell Tissue Research, 224(2): 269-290, 1982.
Thorington et al. "Control of Cnida Discharge: I. Evidence for Two Classes of Chemoreceptor", Biological Bulletin, 174: 163-171, 1988.
Verma et al. "The Achilles Heel of Gene Therapy", Genes and Resistance to Diseases, p. 148, 2000.
Wang et al. "Isolation and Characterization of A Mini-Collagen Gene Encoding a Nematocyst Capsule Protein From a Reef-Building Coral, Acropora Donei", Gene, 152(2): 195-200, 1995. Abstract.
Watson et al. "Cnidocyte Mechanoreceptors Are Tuned to the Movements of Swimming Prey by Chemoreceptors", Science, 243: 1589-1591, 1989.
Watson et al "Receptors for N-Acetylated Sugars May Stimulate Adenylate Cyclase to Sensitize and Time Mechanoreceptors Involved in Triggering Nematocyst Discharge", Experimental Cell Research, 198(1): 8-16, 1992.
Weber "Nematocysts (Stinging Capsules of Cnidaria) as Donnan-Potential-Dominated Osmotic Systems", European Journal of Biochemistry, 184(2): 465-476, 1989.
Weber et al. "Some Physical and Chemical Properties of Purified Nematocysts of Hydra Attenuata Pall. (Hydrozoa, Cnidaria)", Comparative Biochemistry and Physiology, 88B(3): 855-862, 1987.
Westfall et al. "Ultrastructure of the Dinoflagellate Polykrikos. I. Development of the Nematocyst-Taeniocyst Complex and Morphology of the Site for Extrusion", Journal of Cell Science, 63: 245-261, 1983.
Wittlieb et al. "Transgenic *Hydra* Allow in Vivo Tracking of Individual Stem Cells During Morphogenesis", PNAS, Early Edition: 1-4, 2006.
Official Action Dated Sep. 21, 2011 From the US Patent and Trademark Office Re. U.S. Appl. No. 12/955,990.
Response Dated Oct. 17, 2011 to Official Action of Sep. 21, 2011 From the US Patent and Trademark Office Re. U.S. Appl. No. 12/955,990.
Response Dated Jun. 14, 2011 to Official Action of Apr. 11, 2011 From the US Patent and Trademark Office Re.: U.S. Appl. No. 11/374,969.
Restriction Official Action Dated Dec. 2, 2011 From the US Patent and Trademark Office Re. U.S. Appl. No. 12/588,368.

Official Action Dated Jan. 9, 2012 From the US Patent and Trademark Office Re. U.S. Appl. No. 12/955,990.

Summons to Attend Oral Proceedings Pursuant to Rule 115(1) EPC Dated Feb. 16, 2012 From the European Patent Office Re.: Application No. 01976586.6.

Official Action Dated Feb. 16, 2012 From the US Patent and Trademark Office Re. U.S. Appl. No. 12/588,368.

Engel et al. "A Switch in Disulfide Linkage During Minicollagen Assembly in *Hydra* Newmatocysts", The EMBO Journal, 20(12):3063-3073, 2001.

Official Action Dated Jun. 5, 2012 From the U.S. Appl. No. 12/588,368.

Official Action Dated Jul. 3, 2012 From the U.S. Appl. No. 12/955,990.

USE OF STINGING CELLS/CAPSULES FOR THE DELIVERY OF ACTIVE AGENTS TO KERATINOUS SUBSTANCES

RELATED APPLICATIONS

This application is a divisional of U.S. patent application Ser. No. 12/616,801 filed on Nov. 12, 2009, which is a continuation of U.S. patent application Ser. No. 11/328,221 filed on Jan. 10, 2006, now U.S. Pat. No. 7,632,522, which is a continuation-in-part of U.S. patent application Ser. No. 10/868,802 filed on Jun. 17, 2004, now U.S. Pat. No. 7,338,665, which is a divisional of U.S. patent application Ser. No. 10/406,202 filed on Apr. 4, 2003, now U.S. Pat. No. 6,923,976, which is a divisional of U.S. patent application Ser. No. 09/963,672 filed on Sep. 27, 2001, now U.S. Pat. No. 6,613,344, which claims the benefit of priority of U.S. Provisional Patent Application No. 60/235,910 filed on Sep. 28, 2000. The contents of all of the above applications are incorporated by reference as if fully set forth herein.

FIELD AND BACKGROUND OF THE INVENTION

The present invention relates to novel compositions comprising stinging cells or capsules and methods of using same.

Keratin is a fibrous protein that serves as a structural unit for various living tissues. Keratin is the major protein component of hair, wool, nails, horn, hoofs, and the quills of feathers. It contains large quantities of the sulfur-containing amino acids, particularly cysteine. The formation of a disulfide bridge between the sulfur atoms on two cysteines on separate polypeptide chains of keratin allows for the cross-linkage of these chains and results in a fairly rigid aggregate. This phenomenon is consistent with the physiological role of keratin, which provides a tough, fibrous matrix for the tissues in which it is found.

Anatomically, hair comprises three layers, namely, the medulla, cortex and cuticle. The cuticle is the outermost surface of the hair shaft and is composed of a very hard keratinous substance. It consists of flattened platelets of amorphous keratin, wrapped around the hair shaft in several layers, each layer overlapping the adjacent one, progressing from the root to the tip of the hair. A cross section of each cuticle scale reveals that it is sub-divided into three further layers, the endocuticle, exocuticle and epicuticle respectively, the latter one being the outermost layer.

The medulla is the innermost layer of the hair and is composed of a soft keratin-rich material and its occurrence in human hair appears to be variable, usually being present in large thick hairs. Lastly, the cortex is the inner bulk of the hair, which forms the main body of the hair. The cortex is disposed between the medulla and the cuticle. It is composed of a soft, fibrous, crystalline keratin. It provides strength, color and texture to the hair.

Long-lasting treatment of hair requires that therapeutic and cosmetic agents traverse the cuticle and penetrate the cortex in order to react with the keratin inside it and the medulla. Typically, this is achieved by increasing the temperature, or application of an alkaline lotion such as ammonia, both of which serve to separate the scales of the cuticle enough to allow the chemicals to pass through. After the treatment is finished the scales gradually close up again.

However, if hair is processed too many times the cuticle scales may never return to their original tightness and the protection they once offered is lost. The hair becomes increasingly porous, and water can then pass in and out of the cortex. Over-porous hair is dry, and tends to develop split ends. The damaged cuticle is fragile, and the damage worsens as time goes by. The greater the damage, the more the cortex swells with water whenever the hair is washed, but the more water it loses when it dries. The repeated wetting and drying of the cortex gradually weakens the hair.

Ammonia has an additional disadvantageous since it is a reducing agent and breaks sulfur bridges inside the hair. The elasticity of the hair is dependent on a particular sum of sulfur bridges so that if the ammonia treatment is too harsh, the hair will lose more sulfur bonds than necessary causing the hair to harden, lose weight and diameter.

Anti-parasitic agents used to treat the hair are generally provided topically and are rinsed out with water. Thus, their toxic effects last only for the amount of time that the agents are left in the hair. Recurrence of infection is high since it is very difficult to kill all the parasites at all stages of their life cycle.

Fungal infections of the nail are common throughout the world. An estimated 2-13% of the population is affected in North America, with at least 15-20% of those aged 40-60 having one or more fingernails or toenails infected. Toenails are much more commonly affected than fingernails. Infections can range from superficial, causing little more than discoloration, to severe, resulting in loss of the nail together with deformities of the surrounding digit. The incidence of nail fungal infections has been rising over the past few decades, due to factors such as an increased elderly population, increased participation in vigorous physical activity while wearing moisture-retaining shoes and socks, an increase in the number of HIV infected individuals, an increased incidence of diabetes, and increased use of steroids, antibiotics, and other therapeutics that can suppress immunologic responses to fungi.

While nail fungus is rarely life threatening, it causes significant pain, inconvenience, embarrassment, emotional distress, and limitations to manual performance and ambulation. Individuals with moderate to severe nail fungal infections can lose their ability to perform many routine tasks (such as fastening buttons, picking up small objects, walking significant distances) and can lose the ability to perform satisfactorily in their occupations. Due to the unpleasant appearance of their hands or feet, these individuals may become socially self-conscious and embarrassed, and may avoid intimate or other close contact with people. Loss of self-esteem, anxiety, and depression commonly result from moderate to severe cases of fungal nail infection.

At present, topical treatments for nail fungus are rarely effective. Although some oral antifungal therapies have moderate efficacy, they also pose significant risks of toxic reactions, and many patients would prefer local treatments to systemic treatments.

There thus remains a need for improved methods and devices for delivery of therapeutic and cosmetic agents into keratinous substances such as the hair and nail.

"Stinging cells" (e.g. cnidocytes, nematocytes and the like) or "stinging capsules" (e.g., cnidocysts, nematocysts and polar capsules) isolated therefrom have been proposed as suitable agents for tissue delivery of a therapeutic or cosmetic agents [U.S. Pat. Nos. 6,923,976 and 6,613,344 and U.S. Pat. App. No. 20040224013]. Cnidaria (hydras, sea anemones, jellyfish and corals) are aquatic animals, which possess a variety of compounds which are stored and delivered via specialized capsules (cnidocysts), which form a part of specialized cells termed stinging cells (cnidocytes, nematocytes, ptychocytes and the like). The stinging capsules are hard and dense and filled with liquid containing a highly folded, inverted tubule which may also feature specialized structures such as shafts, barbs, spines, and/or stylets. In nature, the cnidocyst discharges and releases its tubule into tissue following physical or chemical triggering.

Discharge is initiated by a rapid osmotic influx of water which generates an internal hydrostatic (liquid) pressure of 150 atmospheres forcing capsule rupture and ejection of the tubule [Holstein, T., and Tardent, P. (1984) *Science*, 223(4638), 830-3]. During ejection, the long coiled and twisted tubule is averted and its length increases by 95%. Accelerating at 40,000 g, the tubule untwists to generate a torque force, which rotates the tubule several times around its axis. These mechanical processes generate a powerful driving force, which enables efficient delivery of the compounds, the toxins and enzymes stored within the capsule [Lotan et al., 1995 *Nature*, 375(6531), 456: Lotan et al., 1996 *J Exp Zool*, 275(6), 444-51; Tardent 1995, *BioEssays*, 17(4), 351-362]. This process, which occurs within microseconds, is among the most rapid exocytosis events in biology [Holstein, T., and Tardent, P. (1984) *Science*, 223(4638), 830-3].

The Cnidaria family which encompasses 10,000 known species includes sedentary single or colonial polyps and pelagic jellyfish. In some of these species, cnidocytes account for more than 45% of the cells present [Tardent 1995, *BioEssays*, 17(4), 351-362].

There are at least three dozen known types of cnidocysts (also termed cnidae) including more than 30 varieties of nematocysts found in most Cnidaria and spirocysts, and ptychocysts found mainly in the Cnidaria class Anthozoa [Mariscal 1974, *Coelenterate biology: reviews and new perspectives*, Academic Press, New York.].

U.S. Pat. Appl. No. 20040224013 and U.S. Pat. Nos. 6,923,976 and 6,613,344 to the present author teach use of stinging cells for in vivo administration of an active agent into the hair follicle via the skin of the scalp and into the nail via the skin of the cuticle. Penetration of living skin tissue, as taught by U.S. Pat. Appl. No. 20040224013 and U.S. Pat. Nos. 6,923,976 and 6,613,344, as opposed to the dead cells of the hair shaft or nail, limits the number of active agents which may be used. Furthermore, for local treatment it is preferred not to treat the skin as the active agents may enter the systemic circulation thereby increasing the incidence of adverse side effects. Penetration into the skin may also be associated with pain. In addition, some treatments, such as hair dyes and anti-parasitic, anti insect agents are not effective when delivered via the skin.

There is thus a widely recognized need for, and it would be highly advantageous to have a non-harmful and non-invasive method of treating keratinous substances such as hair and nails.

SUMMARY OF THE INVENTION

According to one aspect of the present invention there is provided a method of delivering an active agent into a keratinous substance, the method comprising applying a composition comprising the active agent disposed in or around at least one stinging capsule to an outer surface of a non-skin keratinous substance and triggering a discharge of the at least one stinging capsule to thereby deliver the active agent into the non-skin keratinous substance.

According to another aspect of the present invention there is provided a method of delivering an active agent into a keratinous substance, the method comprising applying a composition including, at least one active agent onto an outer surface of a non-skin keratinous substance, applying at least one stinging capsule to the outer surface of the non-skin keratinous substance and triggering a discharge of the at least one stinging capsule to thereby deliver the active agent into the keratinous substance.

According to yet another aspect of the present invention there is provided a method of delivering an active agent into a keratinous substance, the method comprising preconditioning a non-skin keratinous substance by administering into the non-skin keratinous substance at least one stinging capsule and triggering a discharge of the at least one stinging capsule to thereby deliver tubule of the at least one stinging capsule into the non-skin keratinous substance thus preconditioning the non-skin keratinous substance for subsequent delivery of the active agent and subsequently administering the active agent onto the non-skin keratinous substance, thereby effecting the delivery of the active agent into the keratinous substance.

According to further features in preferred embodiments of the invention described below, the active agent and the active substance are identical.

According to still further features in the described preferred embodiments the active agent and the active substance are non-identical.

According to still another aspect of the present invention there is provided a composition of matter comprising an agent beneficial to a non-skin keratinous substance and at least one stinging capsule.

According to further features in preferred embodiments of the invention described below, the active agent is a therapeutic agent.

According to still further features in the described preferred embodiments the therapeutic agent is selected from the group consisting of a drug, an antiparasitic agent, a nucleic acid construct, a vaccine, a hormone, an enzyme and an antibody.

According to still further features in the described preferred embodiments the active agent is a cosmetic agent.

According to still further features in the described preferred embodiments the cosmetic agent is selected from the group consisting of a dye, a vitamin, a perfume, a fragrance, a sun screen and a conditioner.

According to still further features in the described preferred embodiments the keratinous substance is selected from the group consisting of a hair shaft, a nail and a horn.

According to still further features in the described preferred embodiments the composition is formulated in a topical composition selected from the group consisting of a powder, a gel, a cream, an ointment, a paste, a lotion, a milk, a suspension, an aerosol, a spray, a foam and a serum.

According to still further features in the described preferred embodiments the topical composition is administered onto the non-skin keratinous substance using an applicator.

According to still further features in the described preferred embodiments the topical composition further comprises an orientation and proximity agent.

According to still further features in the described preferred embodiments the agent beneficial to a non-skin keratinous substance is a therapeutic agent or a cosmetic agent.

According to still further features in the described preferred embodiments the therapeutic agent is selected from the group comprising an anti-lice/nit agent, an anti-dandruff agent and an antifungal agent, an anti-insect agent and an anti-bacterial agent.

According to still further features in the described preferred embodiments cosmetic agent is selected from the group consisting of a hair dye, a sun-screen, a nail dye, a fragrance and a hair perfume.

The present invention successfully addresses the shortcomings of the presently known configurations by providing a method of penetrating keratinous substances, such as hair and nails, for the delivery of active agents.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

The present invention is of novel compositions comprising stinging cells or capsules and methods of using same.

Specifically, the present invention can be used for delivering active agents into a keratinous substance such as a hair shaft or a nail.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

To treat keratinous substances, such as hair and nails in a long-lasting way, therapeutic and cosmetic agents must traverse the tough outer keratinous layers and penetrate the inner layers. For hair, this is typically achieved by increasing the temperature, or application of an alkaline lotion such as ammonia, both of which serve to separate the scales of the cuticle enough to allow the chemicals to pass through. Both these treatments however, are potentially harmful to both the condition and appearance of the hair.

Nails are treated by topical or systemic application of a therapeutic agent (e.g. anti-fungal agent). At present, topical treatments, however are rarely effective. Although some oral antifungal therapies have moderate efficacy, they also pose significant risks of toxic reactions, and many patients would prefer local treatments to systemic treatments.

The use of stinging capsules/cells from Cnidaria as a means of delivering active agents to the hair and nail through the skin is described in U.S. Pat. App. No. 20040224013, and U.S. Pat. Nos. 6,613,344 and 6,923,976 to the present inventor. Penetration of living skin tissue, as opposed to the dead cells of the hair shaft or nail, limits the number of active agents which may be used. Furthermore, for local treatment it is preferred not to treat the skin as the active agents may enter the systemic circulation thereby increasing the incidence of adverse side effects. Penetration into the skin may also be associated with pain. In addition, some treatments, such as hair dyes and anti-parasitic agents are not effective when delivered via the skin.

While reducing the present invention to practice, the present inventor has uncovered that stinging capsules/cells can penetrate keratinous substances such as hair and nails and thus can be used for the direct delivery of agents into these substances. By penetrating the outer layer of the keratinous substance, active agents applied using stinging capsules may be more effective at either treating a disease or disorder, or having a cosmetic effect. In addition, the use of stinging capsules/cells for administration of an active agent allows the outer layers of the keratinous substances to be exposed to a prolonged treatment since the active agent will not be rinsed out. Release of the active agent from the inner layers to the outer layers of the keratinous substance will typically be slow due to the inherent nature of the keratinous substance. Slow release of an active agent minimizes the number of applications and time between applications. In addition, slow release enables a prolonged treatment, allowing the active agent to be used as a prophylactic.

Thus, according to one aspect of the present invention there is provided a composition of matter comprising an agent beneficial to a non-skin keratinous substance and at least one stinging capsule.

As used herein, the phrase "a non-skin keratinous substance" refers to a keratin-containing substance which is not skin, disposed as the outermost protective covering of mammals which includes, but is not limited to, a hair shaft, a toenail, a fingernail, a hoof, a claw and a horn. The substance may or may not be part of an organism. The hair may be human hair including but not limited to body hair (such as arm-pit hair), scalp hair, pubic hair, eye brow hair and eye lash hair. The hair may also be mammalian hair such as fur, wool, bristles, spines or quills.

As used herein the phrase "stinging capsules" refers to the capsules (cnidocysts), which are contained in stinging cells. The phrase "stinging cells" refers to the specialized cells (e.g. cnidocytes or nematocytes) present in, for example, all members of the phylum Cnidaria, Myxozoa, and Dinoflagellata. The stinging capsules house the delivery tubule. The stinging capsules act as microscopic syringes and serve as a prey or defense mechanism. The stinging capsule is a hardened dense capsule filled with liquid, containing a highly folded inverted tubule which sometimes features specialized structures such as shafts, barbs, spines, and/or stylets.

The stinging capsule according to the teachings of the present invention can be an isolated stinging capsule or alternatively it can form a part of a stinging cell. In any case, the stinging capsule or cell is derived from an organism of the phylum Cnidaria, Myxozoa, or Dinoflagellata.

The stinging cell or capsule utilized by the present invention is preferably derived from an organism of the class Anthozoa, Hydrozoa or Scyphozoa. More specifically, the stinging cell/capsule utilized by the present invention can be derived from, for example, subclasses Hexacorallia or Octocorallia of the class Anthozoa, (mostly sea anemone and corals), subclasses Siponophora or Hydroida of the class Hydrozoa, or from subclasses Rhisostomeae or Semastomeae of the class Scyphozoa.

Stinging capsules from such organisms include toxins, which are non-toxic to humans, and other mammals. As such, these stinging cells or capsules isolated therefrom are ideally suited for safe and efficient delivery of a therapeutic or cosmetic agent into mammalian tissue.

It will be appreciated that the use of stinging cells from organisms which sequester toxins that are not fatal but cause only minor irritations to, for example, mammals, is also envisioned by the present invention.

In addition, stinging cells from other sources can also be utilized by the present invention provided inactivation of the endogenous toxin is effected prior to use.

Such inactivation can be effected via one of several methods, including but not limited to, temperature or chemical denaturation, enzymatic inactivation or ligand inactivation (e.g., Fab fragment of an antibody).

As is demonstrated in U.S. Pat. No. 6,613,344, toxins endogenous to cnidocysts can be efficiently and easily inactivated by incubating isolated cnidocysts at 45° C. for several hours. Alternatively, incubation at a high temperature of 70-95° C. for several minutes can also be utilized by the present invention.

As demonstrated in U.S. Pat. No. 6,613,344, incubation of cnidocysts at 45° C. for 22 hours does not damage or trigger activation of the cnidocyst. Such conditions are effective in denaturing polypeptides stored within the cnidocyst, such as the polypeptide toxins and enzymes delivered by the tubule of the cnidocyst. It will be appreciated that since organisms of, for example, the phylum Cnidaria habitat aquatic environments, which are characterized by temperatures well below 30° C., polypeptides stored within their stinging capsules can be denatured via incubation in temperatures well above 30° C.

The stinging cell or the stinging capsule of the present invention can be isolated from a cell extract prepared from organs or parts of an organism, which contain the stinging cells (for example a whole hydra, tentacles or filaments). Alternatively, stem cells, which give rise to cnidocytes or cnidocysts, can be isolated and cultured or utilized directly.

The main differences between the stinging cells are in their capsule shape and size and in their tubule dimensions. Examples of species containing different tubules include but are not limited to *Rhopilema nomadica* (400 μm hollow tubule length with tiny hollow barbs), *Hydra vulgaris, Hydra hymanae, Metridium senile* (200 μm tubule length), *Nematostella vectensis* (200 μm tubule length), *Rhodactis rhodostoma* (9 mm tubule length), *Heliofungia actiniformis* (1000 μm tubule length) and *Aiptasia diaphana* (150 μm tubule length).

It will be appreciated that organs, tentacles, or parts of an organism, and the whole organism (hydra for example), which contain the stinging cells can be used without the need for prior isolation of individual stinging cells or for isolation of the capsules from the cells.

As is mentioned hereinabove, the compositions of the present invention also include a therapeutic or cosmetic agent suitable for use in non-skin keratinous tissue.

Such agents can be disposed in or around the stinging cell/capsule. According to one preferred embodiment of the present invention, the therapeutic or cosmetic agent is disposed within the liquid stored in the stinging cell or the stinging capsule. In such a case, the stinging cell or the isolated capsule is loaded with the therapeutic or cosmetic agent via any one of several methods generally known in the art such as, but not limited to, diffusion, electroporation, liposome fusion, microinjection and the like.

Alternatively and according to another preferred embodiment of the present invention, the therapeutic or cosmetic agent is disposed in a liquid surrounding the stinging cell or the isolated capsule. In such a case, the stinging capsule's natural mechanism of osmotically collecting liquid from the environment following triggering pumps the therapeutic or cosmetic agent into the stinging cell just prior to or during the discharge. Since the surrounding liquid is pumped into the cnida under extremely high pressures over a short period of time it is highly plausible that high molecular weight molecules, such as polypeptides polynucleotides and other complex molecules can penetrate the capsule and be delivered via the tubule upon discharge.

In any case, since a stinging capsule is highly permeable to water and molecules, therapeutic or cosmetic agent loading prior to or during discharge can be easily achieved.

Prior art studies which concentrated on deciphering the permeability and functionality of stinging capsules have shown that alkali ions, monovalent ions, divalent ions, or small organic cations such as Tris+ or choline+, penetrate cnidocysts and accumulate inside without affecting the properties of the stinging cell or capsule. Studies performed by Lubbock & Amos in order to understand the effect of calcium on capsule discharge (1981) have shown that in the predischarged state the cnida wall is permeable to water and to charged molecules of relatively low molecular weight like bromophenol blue (MW 670) and fluoresceinate (MW 376). Hidaka, who investigated of the mechanism of capsule discharge (1992, 1993), demonstrated that cnidocysts stained with toluidine blue (MW 306) released the blue stain through the tubule when discharged leaving the capsule completely clear.

Thus, short polypeptides, hormones, or any low molecule weight agents can be loaded into stinging cells through simple diffusion. These active compounds can be stored in the stinging capsule and injected into the target substance upon discharge.

Examples of therapeutic agents beneficial to hair include, but are not limited to anti lice agents, an anti-nit agents (or combination thereof) other anti-insect agents, or anti-dandruff agents. Examples of anti-lice/anti-nit agents are pyrethroid-based pediculicides, lindane and malathion.

A therapeutic agent beneficial to nails may be an antifungal agent, an antibacterial agent or an antiviral agent. Examples of anti-fungal agents which may be used according to this aspect of the present invention include, but are not limited to Polyenes (e.g. Nystatin), Imidazoles (e.g. Clotrimazole, Econazole, Ketoconazole, Miconazole, fluconazole and itraconazole), terbinafine, ciclopirox, griseofulvin, and Thiocarbamates (e.g. Tolciclate and Tolnaftate).

Examples of hair cosmetic agents which may be used according to this aspect of the present invention include, but are not limited to a hair dye, a hair conditioner, a vitamin, amino acids, a sun-screen (including chemical, biological and physical sun screens and filters), an antiperspirant, a deodorant and a perfume or fragrance.

Examples of nail cosmetic agents which may be used according to this aspect of the present invention include, but are not limited to, a nail dye, a nail growth promoter, a nail hardener and a nail strengthener and a perfume or fragrance.

The compositions of the present invention may further comprise an orientation and proximity agent.

The orientation and proximity agent is selected for positioning at least one stinging capsule/cell in intimate proximity with the keratinous substance and orientating it such that the opening tip of the stinging capsule (termed the operculum) from where the tubule discharges substantially faces the keratinous substance.

As used herein, the phrase "in intimate proximity with the substance" refers to a range of distances from touching the substance to the furthest distance from the substance that the tubules are still able to penetrate.

As described in U.S. patent application Ser. No. 11/108,662, the stinging capsules have asymmetric charge/structure characteristics, such that the opening tip is positively charged and the opposite end is not. Thus, by using specific agents capable of binding to the opening tip on one hand and a keratinous substance on the other, the capsules can be orientated so that a high proportion of stinging cells come into physical contact with a keratinous substance, thereby enhancing subsequent delivery of an active agent. Specifically, the opening tip is orientated, such that it substantially faces the keratinous substance. The term "substantially facing the keratinous substance" as used herein describes any angle of the opening tip which will allow penetration of the tubule into the keratinous substance. Preferably, the opening tip may be perpendicular to the tissue surface (at an angle of 90°) allowing for the greatest surface area of the opening tip to be in touch with the substance's surface. However, the opening tip may also be orientated at other angles to the keratinous substance.

Preferably, the orientation and proximity agent is a negatively charged polymer, or at least partially negatively charged, which interacts with the positively charged opening tip. Examples of negatively charged polymers that may be used in the present invention include, but are not limited to synthetic anionic polymers such as polyacrylic acid (PAA), poly saccharines, such as alginic Acid, Na alginate, hydroxy propyl methyl cellulose, carboxy methyl cellulose, and others poly saccharines such as gum karaya, gum tragacanth, poly ethylene oxide, poly vinyl alcohol, starch, lecithin. The orientation and proximity agent can be amphoteric for example gelatin, caseine and lecitin. The orientation and proximity agent may also serve as an adhesive or bioadhesive e.g. PAA, carbomer, lectin, bacterial fimbrins and invasins. The capsules can be pretreated with the orientation and proximity agents. Alternatively, the orientation and proximity agents can be introduced into the composition in which the capsules are formulated.

The compositions of the present invention may alternatively or further comprise conditioning agents which increase the porosity of the keratinous substance.

The compositions of the present invention are typically applied topically onto the keratinous substances e.g. in a gel. In this way, the number of tubules need not be limited to one particular area of the substance as is the case with a chip or an array, but may be spread over larger areas. This may be particularly useful when applying active agents to treat the hair, for example in treating lice or when applying cosmetic agents to color or condition the hair.

Alternatively, as described herein below, for more accurate dosing of an active agent, the stinging capsules can be applied onto a keratinous substance using an applicator such as a patch, a cap, a foil, a plaster, a polymer or a pad which can be prepared with an exact quantity of stinging capsules.

To stabilize the stinging cells/capsules and to possibly enhance triggering efficiency, the stinging cells/capsules of the present invention are preferably included in a pharmaceutical composition. Such pharmaceutical compositions comprise a carrier. The carrier generally should not affect the ability of the stinging cells to discharge following triggering. The pharmaceutical compositions of the present invention are generally formulated for topical applications. Examples of pharmaceutical compositions suitable for topical applications include, but are not limited to powders, gels, creams, ointments, pastes, lotions, milks, suspensions, foams and serums.

Thus, according to the teachings of the present invention stinging cells or stinging capsules can be utilized for the in vivo or ex vivo delivery of a therapeutic or cosmetic agent into a keratinous substance.

Delivery of a therapeutic or cosmetic agent according to the present invention can be effected by applying a composition comprising stinging cells and an active agent such as those described above to an outer surface of the keratinous substance (e.g., hair). Following application, the stinging cells or the isolated capsules are triggered (as is further described hereinbelow) and the therapeutic or the cosmetic agent is thereby delivered by the tubule into the substance.

Alternatively, the therapeutic or cosmetic agent can be applied onto the outer surface of the keratinous substance, followed by application of stinging cell(s) or stinging capsules to the same region. Upon triggering, the agent is pumped into the stinging cells or into the capsules (as is further described herein) and the therapeutic or the cosmetic agent is delivered via the tubule into the keratinous substance.

Still alternatively, the outer surface of the keratinous substance can be preconditioned (using either standard delivery methods or stinging cells/capsules) so that it is more amenable to the diffusion through it of active agents. This is effected by tubules which remain in the keratinous substance following stinging capsule/cell discharge. The tubules serve as open channels for subsequent delivery of active agents. According to this aspect of the present invention, the tubules may be preloaded with an active substance which may or may not be identical to the active agent which is subsequently delivered.

As used herein the phrase "triggering a discharge" refers to the activation of at least one stinging capsule/cell whereby the tubule contained within is released and penetrates the keratinous substance. This may be triggered by the active agent itself or by a second agent either by hydration, a change in pH, by a biochemical change (e.g. an enzyme) or by a chemical change.

Chemical triggering can be mediated by substances such as free and conjugated N-acetylated sugars or low molecular weight amino compounds which are known to be detected by at least two classes of stinging cell chemoreceptors. Sodium thiocyanate (NaSCN) is capable of triggering discharge of cnidocysts.

In addition, Lubbock and Amos [Nature, 290(5806), 500-1, 1981] have shown that isolated cnida (cnidocysts) can discharge normally when placed in buffered EGTA or 10 mM citrate solution; Weber [*Eur J Biochem,* 184(2), 465-76 (1989)] demonstrated the effect of dithioerthritol or proteases on discharging isolated cnida and Hidaka [*Advances in Comparative and Environmemtal Physiology,* 15, 45-76 (1993)] discussed various agents which can trigger cnida discharge.

Alternatively, discharge may be effected by hydration with a water-based composition such as saline or water, thereby opening channels in the keratinous substance and enhancing delivery of a subsequent topically applied agent.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Penetration into Hair

Methods and Materials

Stinging capsules in a topical formulation (2% Hydroxypropyl cellulose in ethanol) were applied to human hairs. The treated hairs were immersed in water solution containing 0.05% toluidine blue for activation and better visualization of the stinging capsules. Following activation, the hairs were thoroughly washed with water. The hairs were observed under a stereoscope.

Results

Figure 1:
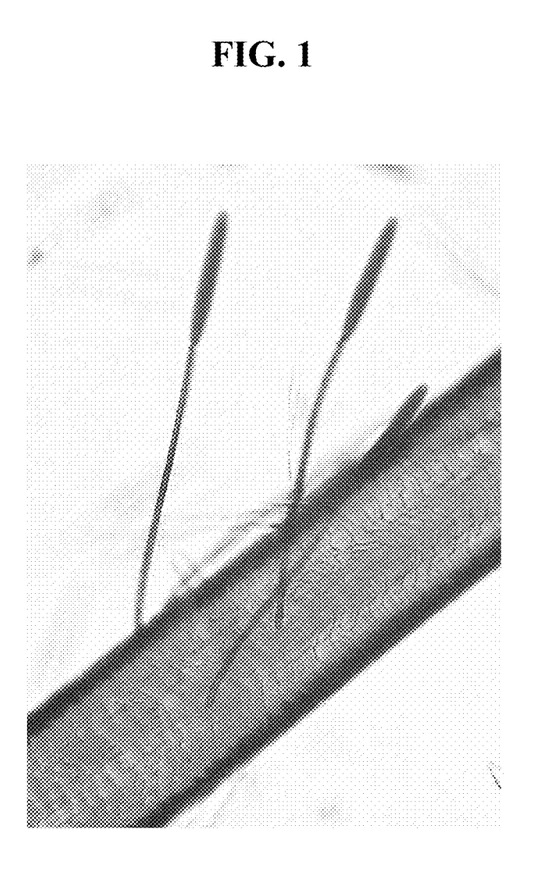
FIG. 1 is a photomicrograph of a hair strand penetrated by stinging tubules.

As illustrated in FIG. 1, the stinging capsules penetrated the hair. Penetration was immediate.

Example 2

Penetration into Nails

Methods and Materials

Stinging capsules in a topical formulation (2% Hydroxypropyl cellulose in ethanol) were applied to human finger and toe nail plates. The treated nails were immersed in water solution containing 0.05% toluidine blue for activation and better visualization of the stinging capsules. After a few seconds, the nails were thoroughly washed with water. The nails were observed under a stereoscope.

Results

Figure 2:
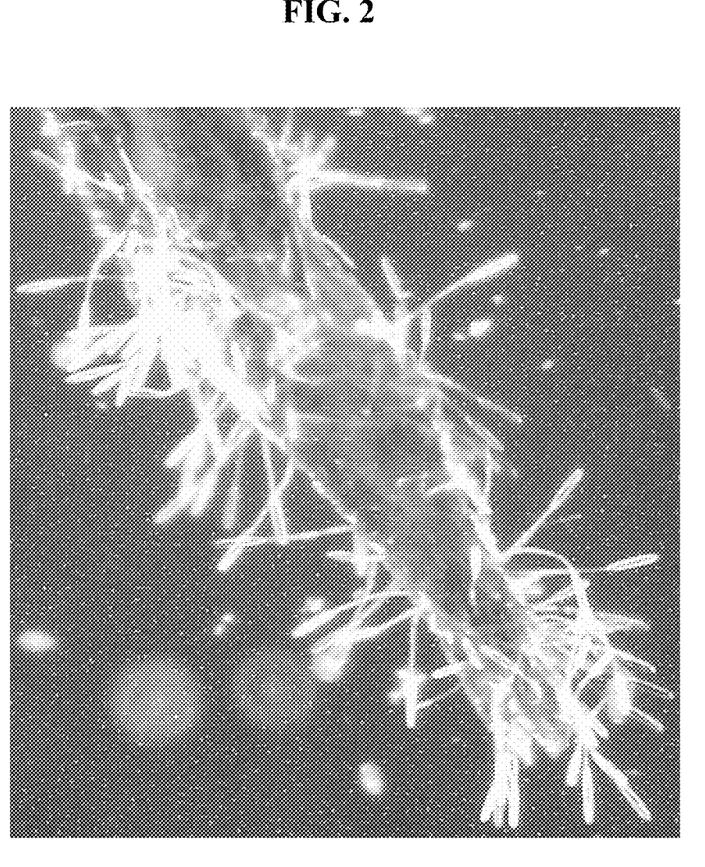
FIG. 2 is a photomicrograph of a nail penetrated by stinging tubules.

As illustrated in FIG. 2, the stinging capsules penetrated the nail.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of delivering an active agent into a hair shaft, the method comprising:
 (a) preconditioning the hair shaft by triggering a discharge of at least one stinging capsule applied to a surface of the hair shaft to thereby deliver tubule of said at least one stinging capsule into the hair shaft, thereby obtaining a preconditioned hair shaft; and
 (b) applying the active agent onto said preconditioned hair shaft, thereby delivering the active agent into the hair shaft,
 wherein said preconditioning is performed before application of said active agent.

2. The method of claim 1, wherein said active agent is a cosmetic agent.

3. The method of claim 2, wherein said cosmetic agent is selected from the group consisting of a dye, a vitamin, a perfume, a fragrance, a sun screen and a conditioner.

4. The method of claim 1, wherein said at least one stinging capsule is formulated in a topical composition selected from the group consisting of a powder, a gel, a cream, an ointment, a paste, a lotion, a milk, a suspension, an aerosol, a spray, a foam and a serum.

5. The method of claim 4, wherein said topical composition is administered onto said hair shaft using an applicator.

6. The method of claim 1, wherein said at least one stinging capsule is from a *Nematostella vectensis*, *Rhopilema nomadica* and *Aiptasia diaphana*.

* * * * *